US009821285B2

(12) United States Patent
Kim et al.

(10) Patent No.: US 9,821,285 B2
(45) Date of Patent: Nov. 21, 2017

(54) C-11 CYANIDE PRODUCTION SYSTEM

(71) Applicant: Brookhaven Science Associates, LLC, Upton, NY (US)

(72) Inventors: Dohyun Kim, Rocky Point, NY (US); David Alexoff, Westhampton, NY (US); Sung Won Kim, North Potomac, MD (US); Jacob M. Hooker, Belmont, MA (US); Richard A. Ferrieri, Patchogue, NY (US)

(73) Assignee: BROOKHAVEN SCIENCE ASSOCIATES, LLC, Upton, NY (US)

( * ) Notice: Subject to any disclaimer, the term of this patent is extended or adjusted under 35 U.S.C. 154(b) by 542 days.

(21) Appl. No.: 14/551,141

(22) Filed: Nov. 24, 2014

(65) Prior Publication Data

US 2015/0217249 A1    Aug. 6, 2015

Related U.S. Application Data

(62) Division of application No. 13/584,033, filed on Aug. 13, 2012, now Pat. No. 8,932,551.

(Continued)

(51) Int. Cl.
*B01J 8/02*     (2006.01)
*B01J 8/04*     (2006.01)
(Continued)

(52) U.S. Cl.
CPC .......... *B01J 8/0285* (2013.01); *B01J 8/0278* (2013.01); *B01J 8/0492* (2013.01); *B01J 8/0496* (2013.01);
(Continued)

(58) Field of Classification Search
CPC ...... B01J 8/0496; B01J 8/0492; B01J 8/0285; B01J 8/0278; B01J 19/02; B01J 2208/00415; B01J 2208/00823; B01J 2208/00893; B01J 2208/024; B01J 2208/025; C01C 3/0229
See application file for complete search history.

(56) References Cited

PUBLICATIONS

Kil, Kun-Eek, "Synthesis of carbon-11 radiopharaceuticals and their evaluations," Dissertation, 2009, ProQuest LLC.*

* cited by examiner

*Primary Examiner* — Lessanework Seifu
(74) *Attorney, Agent, or Firm* — Dorene M. Price

(57) ABSTRACT

A method for providing $^{11}$C-labeled cyanides from $^{11}$C labeled oxides in a target gas stream retrieved from an irradiated high pressure gaseous target containing $O_2$, wherein $^{11}$C labeled oxides are reduced with $H_2$ in the presence of a nickel catalyst under a pressure and a temperature sufficient to form a product stream comprising at least about 95% $^{11}CH_4$, the $^{11}CH_4$ is then combined with an excess of $NH_3$ in a carrier/reaction stream flowing at an accelerated velocity and the combined $^{11}CH4$ carrier/reaction stream is then contacted with a platinum (Pt) catalyst particulate supported on a substantially-chemically-nonreactive heat-stable support at a temperature of at least about 900° C., whereby a product stream comprising at least about 60% $H^{11}CN$ is provided in less than 10 minutes from retrieval of the $^{11}$C labeled oxide.

7 Claims, 4 Drawing Sheets

Related U.S. Application Data

(60) Provisional application No. 61/524,121, filed on Aug. 16, 2011.

(51) Int. Cl.
 *C01C 3/02* (2006.01)
 *C07B 59/00* (2006.01)

(52) U.S. Cl.
 CPC ............ *C01C 3/0229* (2013.01); *C07B 59/00* (2013.01); *B01J 2208/00415* (2013.01); *B01J 2208/00823* (2013.01); *B01J 2208/00893* (2013.01); *B01J 2208/024* (2013.01); *C01C 3/0212* (2013.01); *C01C 3/0216* (2013.01)

*Fig. 6*
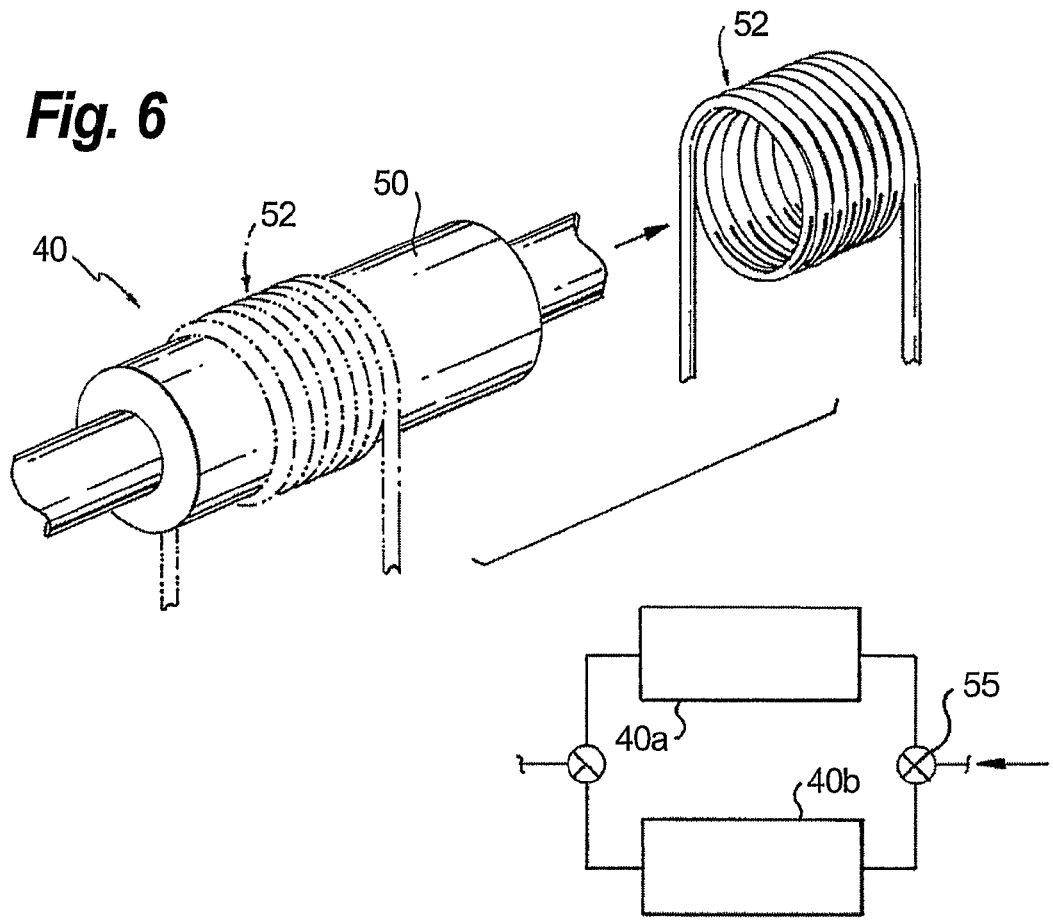
*Fig. 7*
*Fig. 8*
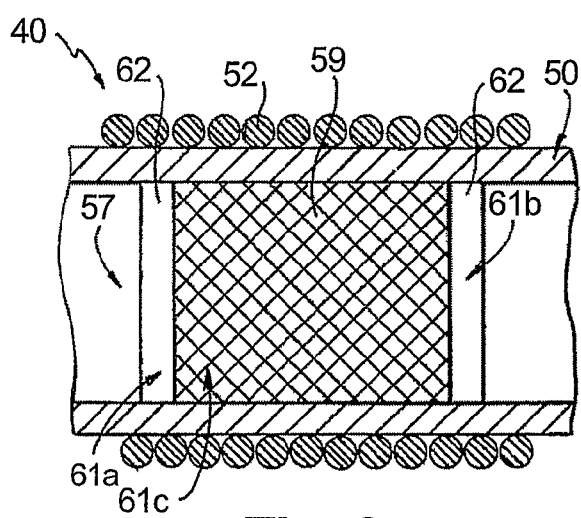

US 9,821,285 B2

C-11 CYANIDE PRODUCTION SYSTEM

CROSS-REFERENCE TO RELATED APPLICATIONS

This application is a divisional of U.S. patent application Ser. No. 13/584,033, filed Aug. 13, 2012, which claims benefit of U.S. Provisional Application Ser. No. 61/524,121, filed on Aug. 16, 2011, the entire contents of both of which are incorporated herein by reference.

STATEMENT OF GOVERNMENT LICENSE RIGHTS

This invention was made with Government support under contract number DE-AC02-98CH10886, awarded by the U.S. Department of Energy and under grant number R21A1084189, awarded by the U.S. National Institutes of Health. The Government has certain rights in the invention.

FIELD OF THE INVENTION

The present invention relates generally to chemical processes for synthesizing radioactive compounds for imaging, such as by positron emission tomography (PET). More particularly, the present invention relates to a compact, stand-alone instrument and method for producing C-11 cyanide ($H^{11}CN$) in a fast and efficient manner.

BACKGROUND

Positron emission tomography (PET) is a molecular imaging technology that is increasingly used for detection of disease. PET imaging systems create images based on the distribution of positron-emitting isotopes in the tissue of a patient. The isotopes are typically administered to a patient by injection of PET radiotracer probe molecules that comprise a positron-emitting isotope, (e.g. carbon-11, nitrogen-13, oxygen-15, or fluorine 18), covalently attached to a molecule that is readily metabolized or localized in the body or that chemically binds to receptor sites within the body. For PET radiotracer probes the short half-lives of the positron emitting isotopes require that synthesis, analysis and purification of the probes are completed rapidly.

Carbon-11 (C-11) cyanide is a highly valuable precursor molecule for PET radiotracer synthesis by chemical transformations such as displacement and cross-coupling reactions. The resulting C-11 cyano-compounds can also be converted to various functional groups such as amines, amides, carboxylic acids, which are abundant in various biological substrates, drugs and radiotracers. Various methods for synthesizing C-11 cyanide are known in the art. However, conventional C-11 cyanide production systems that are currently commercially available are large in size, not stand-alone or not cost-effective.

Moreover, due to the short half-life (20 min) of C-11, a short production time is required. However, the production time involved in typical C-11 cyanide production systems of the prior art leave little remaining time for useful analytic purposes.

Accordingly, there is a need to develop smaller or miniaturized systems and devices that are capable of processing small quantities of molecular probes. In addition, there is a need for such systems that are capable of expediting chemical processing to reduce the overall processing or cycle times, simplifying the chemical processing procedures, and at the same time, provide the flexibility to produce a wide range of probes, biomarkers and labeled drugs, or drug analogs, inexpensively.

SUMMARY

The present method relates to providing $^{11}C$ labeled cyanides from $^{11}C$ labeled oxides in a target gas stream retrieved from an irradiated high pressure gaseous target containing $O_2$. The method generally includes:
  (i) reducing $^{11}C$ labeled oxides with $H_2$ in the presence of a nickel catalyst under a pressure and a temperature sufficient to form a product stream comprising at least about 95% $^{11}CH_4$;
  (ii) combining the $^{11}CH_4$ with an excess of $NH_3$ in a carrier/reaction stream flowing at an accelerated velocity; and
  (iii) contacting the combined $^{11}CH_4$ carrier/reaction stream with a platinum (Pt) catalyst particulate supported on a substantially-chemically-nonreactive heat-stable support at a temperature of at least about 900° C., and more preferably is at least about 940° C., whereby a product stream comprising at least about 60% $H^{11}CN$ is provided in less than 10 minutes from retrieval of the $^{11}C$ labeled oxides.

In a preferred embodiment, the method further includes mixing the $^{11}CH_4$ and $NH_3$ carrier/reactant stream prior to contacting the stream with the Pt catalyst at elevated temperature. The method further preferably includes removing unreacted $^{11}CO_2$ from the product stream resulting from step (i) to provide a cleansed $^{11}CH_4$ product stream of increased $^{11}CH_4$ content. The act of removing preferably includes passing the product stream resulting from step (i) through a soda lime trap whereby $^{11}CO_2$ is scrubbed from the stream.

The act of reducing preferably includes passing a pressurized stream of $^{11}CO_2$, $NH_2$, and $N_2$ through a heated zone packed with a mixture of nickel (Ni) catalyst powder and a molecular sieve, such heated zone having an entrance and an exit. The heated zone is preferably arranged with subzones of substantially all nickel catalyst powder at the entrance of the zone and at the exit of the zone so that the nickel-only subzones sandwich a third subzone which houses the mixture of the nickel powder and the molecular sieve. The molecular sieve is provided in an amount sufficient to trap substantially all of the nonreacted $^{11}CO_2$ present in the pressurized stream for subsequent desorption in the presence of heat for reduction to $^{11}CH_4$.

The act of flowing at accelerated velocity includes passing $NH_3$ gas to the combining of (ii) at a rate of at least about 550 ml/min up to a speed which permits substantially complete reaction of the $^{11}CH_4$ in the combined stream to form $H^{11}CN$. The accelerated velocity for passing the $NH_3$ gas is preferably a rate from about 600 ml/min to about 700 ml/min, and more preferably, a rate from about 640 ml/min to about 660 ml/min.

In a preferred embodiment, the platinum catalyst particulate of (iii) is platinum black and the substantially-chemically-nonreactive heat-stable support is a molecular sieve, which is heat stable up to at least 1500° C.

The present method includes miniaturizing a reaction furnace having a reaction chamber for reacting $^{11}CH_4$ with $NH_3$ to form $H^{11}CN$ in the presence of a platinum catalyst. The method generally includes:
  (i) supporting platinum particulate with a substantially-chemically-nonreactive heat-stable support; and
  (ii) minimizing the size of said reaction chamber for housing said supported platinum particulate to obtain high efficiency $H^{11}CN$ conversion from a reaction stream passed therethrough, said reaction stream comprising substantially $^{11}CH_4$ and $NH_3$, whereby the size of said furnace can be miniaturized.

In a preferred embodiment, the platinum particulate is platinum black and the substantially-chemically-nonreactive heat-stable support is a molecular sieve. The step of minimizing preferably means providing a chamber having a volume not greater than about 30 cubic centimeters.

The present method further involves optimizing the conversion of $^{11}CO_2$ to form $^{11}CH_4$ by reducing $^{11}CO_2$ with $H_2$ using nickel catalyst. The method generally includes:

(i) passing a $^{11}CO_2$ stream with a stream of $N_2$ and $H_2$ under pressure through a chemical reduction zone having an entry and an exit, such zone subdivided into three subzones, an entry subzone, a middle subzone, and an exit subzone, the entry and exit subzones are provided with a substantially only nickel-catalyst powder and the middle subzone is provided with a mixture of nickel catalyst powder and molecular sieve; and (ii) heating the chemical reduction zone to promote such reduction, whereby $^{11}CO_2$ is at least partially reduced in the entry and exit subzone while the substantial balance of $^{11}CO_2$ is absorbed by the molecular sieve and is subsequently desorbed therefrom in the presence of heat and substantially completely reduced in the presence of the nickel powder.

A present system is also provided and relates to producing $H^{11}CN$ gas from $^{11}C$-labeled oxides in less than ten (10) minutes. The present system generally includes a $^{11}CO_2$ inlet conduit for receiving and conveying $^{11}CO_2$ gas from a target, a $H_2$ inlet conduit for receiving and conveying $H_2$ gas from a source, a $N_2$ inlet conduit for receiving and conveying $N_2$ gas from a source, a nickel furnace fluidly connected with the $^{11}CO_2$ inlet, the $H_2$ inlet and the $N_2$ inlet for receiving the $^{11}CO_2$ gas, the $H_2$ gas and the $N_2$ gas respectively therefrom. The furnace heats the $^{11}CO_2$ gas, the $H_2$ gas and the $N_2$ gas in the presence of a nickel catalyst contained therein to produce $^{11}CH_4$ gas. A $^{11}CH_4$ conduit is connected to an outlet of the nickel furnace for receiving and conveying the $^{11}CH_4$ gas from the nickel furnace, a $NH_3$ inlet conduit for receiving and conveying $NH_3$ gas from a source, a platinum furnace fluidly connected with the $^{11}CH_4$ conduit and the $NH_3$ inlet conduit for receiving the $^{11}CH_4$ gas and the $NH_3$ gas respectively therefrom and for heating the $^{11}CH_4$ gas and the $NH_3$ gas in the presence of a platinum catalyst. The platinum furnace produces $H^{11}CN$ gas and a $H^{11}CN$ outlet conduit is fluidly connected to an outlet of the platinum furnace for receiving and conveying the $H^{11}CN$ gas from the platinum furnace. The $^{11}CO_2$ inlet conduit, the $H_2$ inlet conduit, the $N_2$ inlet conduit, the nickel furnace, the $^{11}CH_4$ conduit, the $NH_3$ inlet conduit, the platinum furnace and the $H^{11}CN$ outlet conduit collectively define a total system gaseous volume of about less than 18 mL whereby the system provides a total system cycle time for producing $H^{11}CN$ gas of less than ten (10) minutes. In a preferred embodiment, the system occupies a space less than or equal to about 20 cm×28 cm×27 cm.

Also, the system preferably includes a soda lime trap disposed in the $^{11}CH_4$ conduit for removing unreacted $^{11}CO_2$ gas from the $^{11}CH_4$ conduit. The system preferably further includes a mixer fluidly connected with the $^{11}CH_4$ conduit and the $NH_4$ inlet conduit for respectively receiving and mixing the $^{11}CH_4$ gas and the $NH_3$ gas from the $^{11}CH_4$ conduit and the $NH_3$ inlet conduit.

The nickel furnace preferably includes an alumina tube and an electrical resistance heating wire wrapped around the alumina tube. The alumina tube preferably has a length of about 4.5 cm, an outer diameter of about 1.3 cm and an inner diameter of about 0.95 cm.

The platinum furnace preferably includes an alumina tube and an electrical resistance heating wire wrapped around the alumina tube. The alumina tube preferably has a length of about 15 cm, an outer diameter of about 2 cm and an inner diameter of about 1.6 cm.

The preferred embodiments of the present C-11 cyanide production system and the method for producing C-11 cyanide, as well as other objects, features and advantages of this invention, will be apparent from the following detailed description, which is to be read in conjunction with the accompanying drawings. The scope of the invention will be pointed out in the claims.

BRIEF DESCRIPTION OF THE DRAWINGS

FIG. 6 is a diagrammatic side view of an embodiment for rapidly cooling the nickel furnace of the present invention.

FIG. 7 is a schematic diagram of an alternative embodiment of the present invention, wherein two nickel furnaces are provided in parallel.

FIG. 8 is a diagrammatic cross-sectional view of a preferred embodiment of a nickel catalyst package used in the nickel furnace of the present invention.

DETAILED DESCRIPTION OF THE PREFERRED EMBODIMENTS

Figure 1:
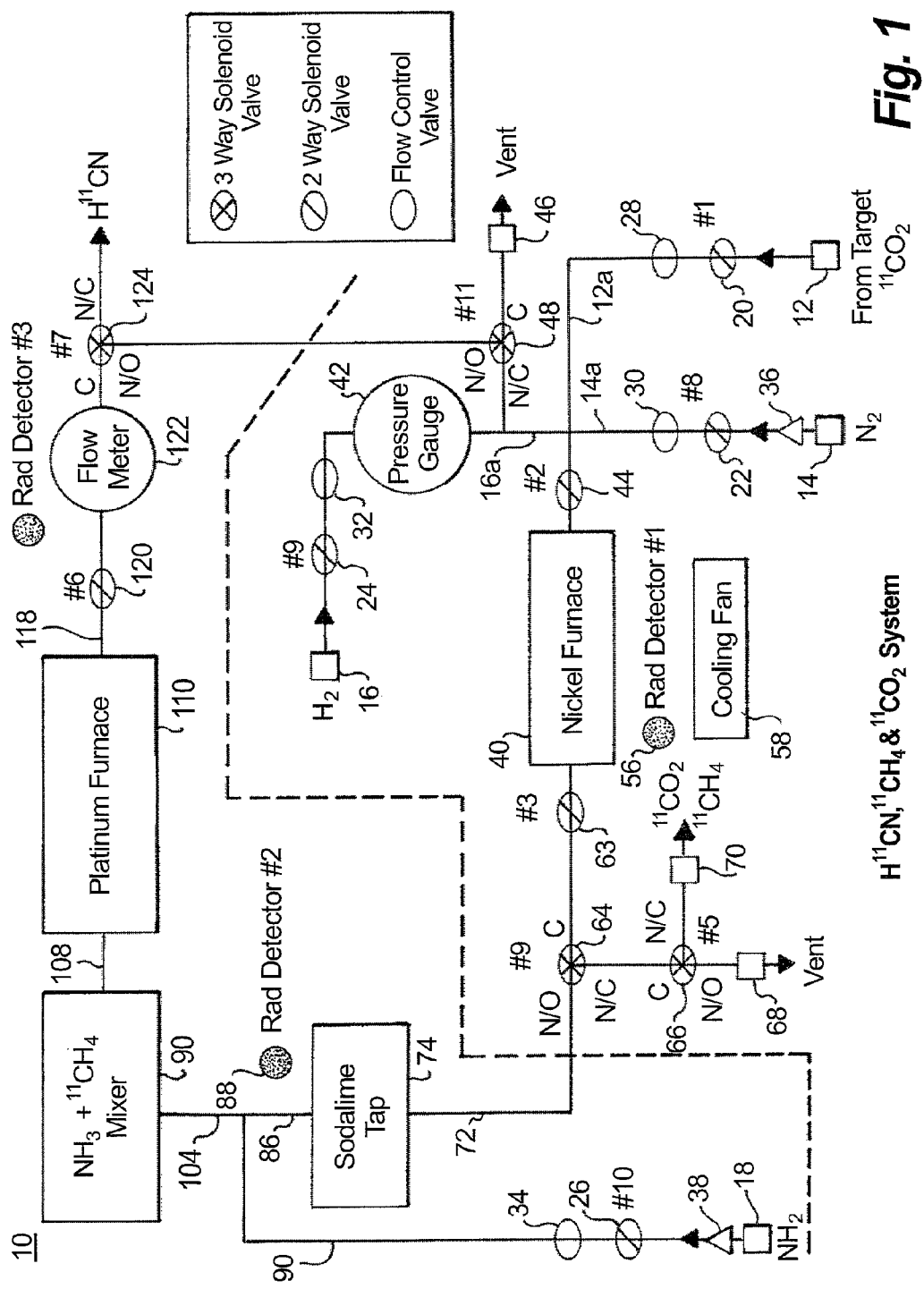
FIG. 1 is a schematic drawing of the present C-11 cyanide production system.

Referring first to FIG. 1, the present system 10 is generally a combination of commercially available and custom design components provided in a miniaturized form in order to provide a compact and efficient system for producing C-11 cyanide ($H^{11}CN$) gas. This system 10 is preferably supported on a compact "mother board" frame or plate (not shown) having overall dimensions of approximately 20 cm (D)×28 cm (W)×27 cm (H). Hardware for attaching the components to the frame or plate preferably take the form of clips or other such brackets fixed to the plate or frame, which allow for quick and releasable plug-in connection of the various components. As a result, easy access and quick replacement of the components is provided with the system 10 of the present invention.

The present system 10 includes four inlet ports 12, 14, 16, 18 for introducing the necessary process gases to the system. The inlet ports 12, 14, 16, 18 are preferably in the form of needle valves, or other type of quick-connect devices for connecting flexible hoses or other conduits from their respective gas sources. Inlet port 12 receives radioactive C-11 carbon-dioxide ($^{11}CO_2$) gas from a target source. Inlet port 14 receives nitrogen ($N_2$) gas from a source. Inlet port 16 receives hydrogen ($H_2$) gas from a source and inlet port 18 receives ammonia ($NH_3$) gas from a source.

Immediately down-stream of each inlet port 12, 14, 16, 18 is a 2-way solenoid valve 20, 22, 24, 26 and a flow control valve 28, 30, 32 and 34 for controlling and regulating the flow of the respective process gas into the system. Also, preferably provided on at least the nitrogen ($N_2$) inlet port 14 and the ammonia ($NH_3$) inlet port 18 are pressure regulators 36, 38 to control the respective pressure of the nitrogen and ammonia gases entering the system.

The solenoid valves, control valves, pressure regulators and needle valves are generally commercially available parts but are selected to provide a small cross-sectional flow. Similarly, the tubing or conduits for conveying the process gases between the various components of the system have a relatively small cross-section of equal to or less than about 0.2 cm to minimize the overall volume of the gas in the system. As a result, the overall flow cycle time is reduced and, as will be discussed in further detail below, the conditioning time (i.e., the time required to initially bring the system to operational condition) can also be reduced.

The C-11 carbon dioxide ($^{11}CO_2$) inlet 12, the nitrogen ($N_2$) inlet 14 and the hydrogen ($H_2$) inlet 16 are all disposed upstream and are fluidly connected to a nickel furnace 40. A pressure gauge 42 is also preferably provided upstream of the nickel furnace for monitoring the pressure of the process gases entering the nickel furnace. The pressure gauge 42 is connected to a vent 46 via a 3-way solenoid valve 48 for venting process gasses should the pressure get too high.

The C-11 carbon dioxide ($^{11}CO_2$) line 12A, the nitrogen ($N_2$) line 14A and the hydrogen ($H_2$) line 16A all preferably meet and feed into a single two way solenoid valve 44 located immediately upstream of the nickel furnace 40. The two way nickel furnace inlet solenoid valve 44 provides for a single shut-off of all gases entering the nickel furnace if required.

Figure 2:
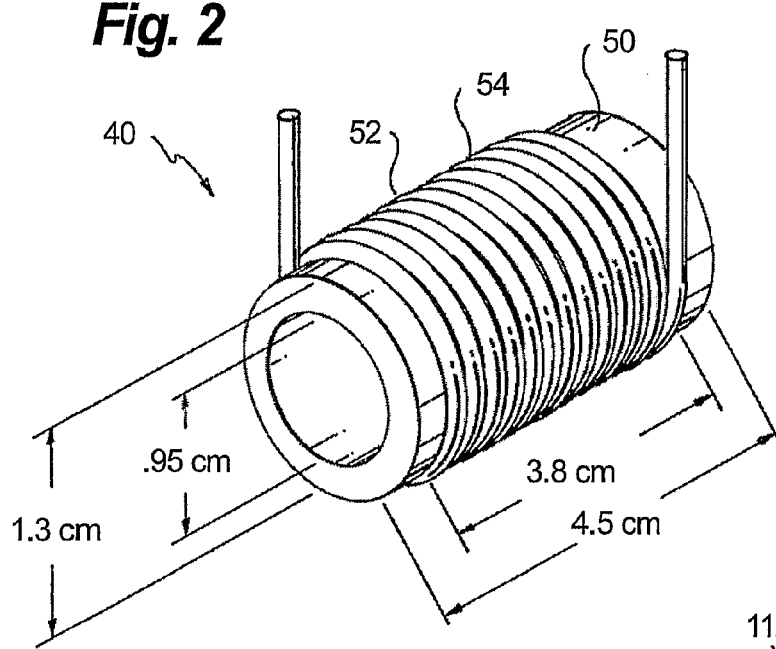
FIG. 2 is a side view of the nickel furnace of the system shown in FIG. 1.

As shown additionally in FIG. 2, the nickel furnace 40 is a custom designed, miniaturized furnace, which permits extremely rapid heat-up and cool-down time, as compared to nickel furnaces used in conventional C-11 cyanide production systems. The nickel furnace 40 includes a commercially available alumina tube 50 having a length of about 4.5 cm, an outer diameter of about 13 mm and an inner diameter of about 9.5 mm. A length of Kanthal A-1® electrical heating wire 52 is tightly wrapped around the outer surface of the alumina tube 50. The wire 52 preferably extends along the central axial length of the tube 50 to create a heating zone 54 having a length of about 3.8 cm. Opposite ends of the wire 52 are preferably provided with electrical terminals or are otherwise exposed to allow for connection to an electric source.

The wire 52 preferably has a resistance of 4.147 ohms/foot to provide a total resistance of 32 ohms. Therefore, providing a current of 3.75 A would produce a heater producing 450 W. With this design, the nickel heater 40 can be heated from room temperature to 400-450° C. in approximately 10-15 seconds.

The electrical heating wire 52 can be fixed to the tube 50 using a commercially available ceramic paste. Alternatively, the wire 52 can be releasable from the tube 50 to enable a rapid cool-down of the tube. In particular, the wire 52 and the tube 50 can be assembled to allow the pre-formed coiled wire to be axially translated away from the tube in order to separate the tube from the still hot wire after the heating process is complete, as shown in FIG. 6. In this manner, the tube 50 will cool down faster than the heating wire, which will provide a quicker cycle time to repeat the process.

Another way to improve cycle time of the system, with respect to the heating and cooling time required for the nickel furnace 40, is to provide the system with two nickel furnaces 40a and 40b in parallel, as shown in FIG. 7. Thus, while one of the furnaces 40a, for example, is in use and being heated, the other furnace 40b is not in use and is being cooled. In this case, a three-way valve 55 is provided to divert the incoming gas to the furnace 40a in use, while the other furnace 40b cools. Once the reaction is complete in the furnace 40a in use, the reacted gas is evacuated and this furnace 40a is allowed to cool down. In the meantime, once the idle furnace 40b is sufficiently cool, the three-way valve 55 switches over to divert gas to this furnace 40b, while the other furnace 40a cools. The result is a dramatic reduction in system down-time, which would otherwise be required to allow a single nickel furnace to cool after each cycle.

In any case, the nickel furnace 40 contains a nickel catalyst, which is used to react the C-11 carbon dioxide ($^{11}CO_2$) gas fed to the furnace. The nickel catalyst is preferably provided in a nickel catalyst package 57, as shown in FIG. 8, which can be inserted into the tube 50 of the nickel furnace 40. The nickel catalyst package 57 is preferably about 2.5-3.0 cm long and is divided into subzones. A central subzone is defined by a molecular sieve 59 and an entrance subzone 61a and an exit subzone 61b are respectively defined by two nickel plugs 62 bounding opposite ends of the sieve 59.

The sieve 59 is preferably a 4 A 80/100 mesh sieve. A suitable molecular sieve for use in the present system is available at Grace Davison Discovery Science—Catalog: 5624 (www.discoverysciences.com). The sieve 59 captures an amount of nickel catalyst powder for trapping un-reacted C-11 carbon dioxide ($^{11}CO_2$) gas. A suitable nickel catalyst powder can be obtained from Shimadzu Corp. under the trade name of Shimalite-Ni (reduced), P/N 221-27719, Lot No. S91461. In a preferred embodiment, about 130 mg nickel powder is captured in 260 mg of nickel sieve.

The nickel plugs 62 are essentially high concentration nickel catalyst powder packed together to form a relatively dense disc-shaped element, as compared to the sieve 59. In a preferred embodiment, each nickel plug 62 contains about 20 mg of nickel powder. This results in a nickel package 57 having a nickel/molecular sieve ratio of about 170 mg/260 mg.

It has been found with conventional nickel catalyst packages, which typically consist of only a molecular sieve containing the nickel catalyst without nickel end plugs, most of the chemical reaction occurs at the gas entrance and exit portions of the sieve. As a result, the ends of conventional nickel catalyst packages are typically depleted of nickel catalyst well before the center portion of the package.

By providing a higher concentration of nickel, in the form of nickel plugs 62, at the entrance and exit regions of the package 57 with the present system on, more efficient use of the nickel catalyst can be achieved. Specifically, the nickel package 57 of the present system optimizes the process of conversion of $^{11}CO_2$ to form $^{11}CH_4$ by reducing $^{11}CO_2$ with $H_2$ using nickel catalyst.

Thus, a $^{11}CO_2$ stream with a stream of $N_2$ and $H_2$ is passed under pressure through the nickel package 57 in the nickel furnace 40, wherein the nickel package forms a chemical reaction zone having an entry and an exit. The chemical reaction zone is subdivided into an entry subzone 61a, a middle subzone 61c, and an exit subzone 61b, wherein the entry and exit subzones are provided with a nickel catalyst powder in a concentrated form (i.e., the nickel plugs 62) and the middle subzone is provided with a mixture of nickel catalyst powder and molecular sieve 59. The chemical reduction zone is then heated to promote the reduction, whereby $^{11}CO_2$ is at least partially reduced in the entry and exit subzone while the substantial balance of $^{11}CO_2$ is absorbed by the molecular sieve and is subsequently desorbed therefrom in the presence of heat and substantially completely reduced in the presence of the nickel powder.

As a result, the package 57 can be made smaller, while providing the same amount of nickel catalyst as compared with conventional nickel catalyst packages. In turn, by making the nickel catalyst package 57 smaller, the nickel furnace 40, and thus the entire system can be made smaller.

Returning to FIG. 1, a first radiation detector 56 and a cooling fan 58 are preferably provided immediately adjacent to the nickel furnace 40. The first radiation detector 56 is provided to monitor un-reacted C-11 carbon dioxide ($^{11}CO_2$) gas in the nickel furnace 40, while the cooling fan 58 is provided to provide for rapid cooling the nickel furnace once the reaction time is complete. With the cooling fan 58 provided, the heat nickel furnace 40 can cool from 450° C. to room temperature in approximately 15 minutes.

Connected to the outlet of the nickel furnace 40 is a nickel furnace outlet line 60 for delivering reacted gas from the nickel furnace further along the system. Preferably provided in the nickel outlet line 60 is a two-way solenoid valve 63 which allows for the control of reacted gas entering the outlet line 60 from the nickel furnace 40. The outlet line 60 further preferably includes a three-way solenoid valve 64 for diverting converted C-11 methane ($^{11}CH_4$) gas and un-reacted C-11 carbon dioxide ($^{11}CO_2$) gas from the system. A second three-way solenoid valve 66 can be provided to further divert the converted C-11 methane ($^{11}CH_4$) gas and/or the un-reacted C-11 carbon dioxide ($^{11}CO_2$) gas to a vent 68 or an access outlet 70.

Figure 3:
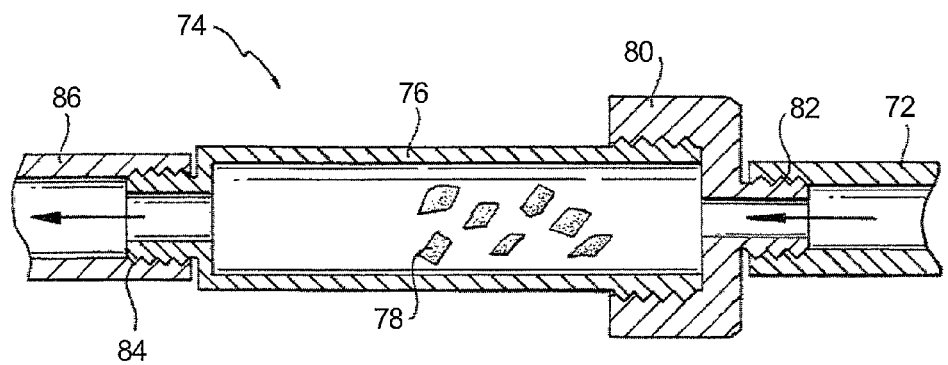
FIG. 3 is a cross-sectional view of the soda lime trap of the system shown in FIG. 1.

The converted C-11 methane ($^{11}CH_4$) gas not diverted from the system 10 is then fed into a sodalime trap inlet line 72, which feeds the C-11 methane ($^{11}CH_4$) gas to a sodalime trap 74. As shown additionally in FIG. 3, the sodalime trap 74 is customized and designed on a miniaturized scale, to remove unwanted C-11 carbon dioxide ($^{11}CO_2$) from the system. The sodalime trap 74 is essentially a narrow tube 76 having an amount of sodalime 78 contained therein. The tube 76 includes a removeable cap 80 threaded at one end of the tube to permit replenishment of the sodalime 78 in the trap 74 as needed. The cap preferably includes an inlet 82 for connection to the sodalime inlet line 72. Provided at the opposite end of the tube 76 is an outlet 84 for connection to a sodalime outlet line 86.

The sodalime trap 74 removes essentially all of the un-reacted C-11 carbon dioxide ($^{11}CO_2$) from the system. In this regard, a second radiation detector 88 is preferably provided adjacent the sodalime trap 74 to monitor any un-reacted C-11 carbon dioxide ($^{11}CO_2$).

The sodalime outlet line 86 meets with an ammonia ($NH_3$) line 90, which feeds ammonia gas from the ammonia inlet 18 to the system. The ammonia ($NH_3$) line 90 and the sodalime trap outlet line 86 feed a mixer 92, which mixes the ammonia ($NH_3$) gas and the C-11 methane ($^{11}CH_4$) gas.

Figure 4:
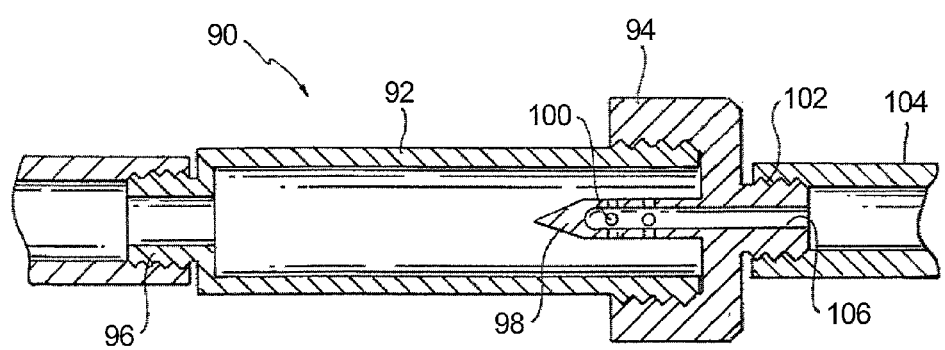
FIG. 4 is a cross-sectional view of the mixer of the system shown in FIG. 1.

As additionally shown in FIG. 4, the mixer 90 is also a custom made part that provides efficient mixing on a small scale. The mixer 90 includes a tube 90 having a cap 94 connected at an inlet end of the tube and an outlet 96 connected at the opposite end of the tube. The cap 94 is preferably connected to the inlet end of the tube 92 via a threaded connection to allow for removal of the cap as needed.

The cap is formed with a needle nozzle 98 which extends into the interior of the tube 92. The needle nozzle 98 is closed at its distal end and is provided with a plurality of apertures 100 through which gas fed into the interior of the nozzle may exit. Extending outwardly from the cap in a direction opposite to the inward direction of the needle nozzle 98 is an inlet port 102 for connection with a mixer inlet line 104, which in turn is connected with the sodalime outlet trap 86 and the ammonia ($NH_3$) inlet line 90. An internal conduit 106 extends from the cap inlet 102 to the needle nozzle 98 and is in fluid communication with the plurality of apertures 100 formed in the needle nozzle. Thus, gas flowing from the mixer inlet line 104 into the mixer 90 exits through the apertures 100 of the needle nozzle 98 into the interior of the tube 92 in a manner which will provide efficient mixing of the ammonia ($NH_3$) and the C-11 methane ($^{11}CH_4$) gases.

Figure 5:
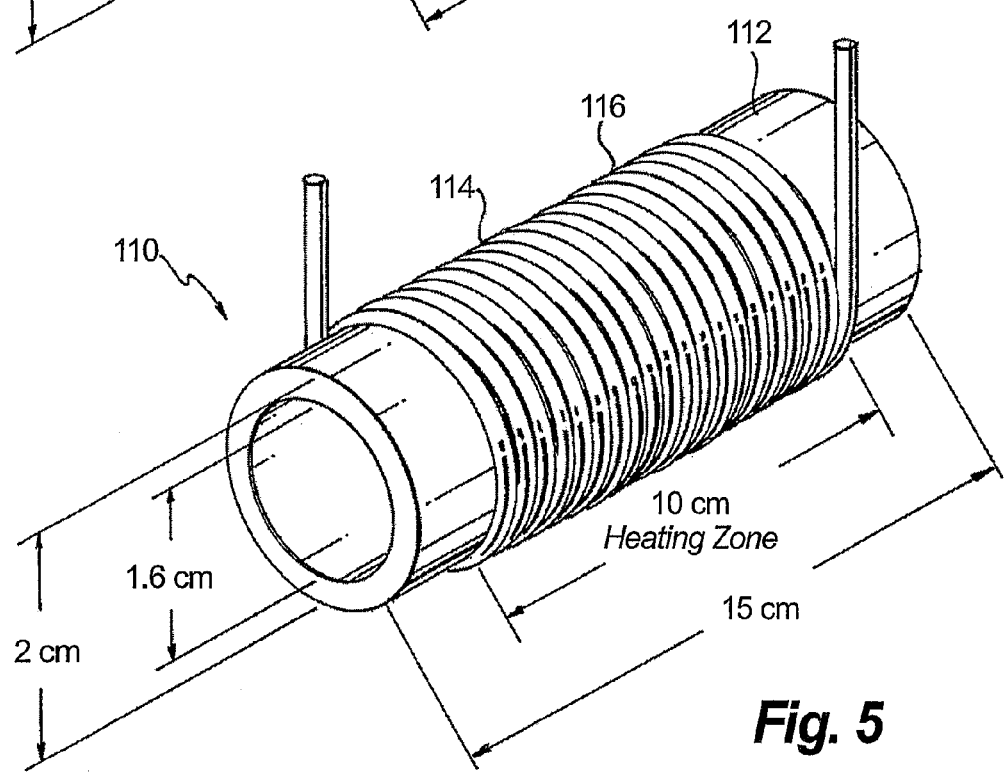
FIG. 5 is a side view of the platinum furnace of the system shown in FIG. 1.

A platinum furnace inlet line 108 is connected to the outlet 96 of the mixer 90 for delivering the mixed ammonia ($NH_3$) and C-11 methane ($^{11}CH_4$) gases to a platinum furnace 110. As shown additionally in FIG. 5, the platinum furnace 110 is also a custom made part designed with the goals of miniaturization and rapid heating in mind. In this regard, the platinum furnace includes a quartz tube 112 wrapped with a Kanthal A-1® electrical heating wire 114. The quartz tube is preferably about 150 mm in length, having an outer diameter of 20 mm and an inner diameter of 16 mm. The wire 114 is wrapped around the outer surface of the quartz tube 112 along a central length of the tube to provide a heating zone 116 of approximately 100 mm in length. The Kanthal A-1® heating wire 114 preferably has a 24 AWG, a length of about 6.8 meters and a diameter of 1 mm. The wire has a maximum operating temperature of between 1350-2460° C. and is applied to the quartz tube 112 with a commercially available ceramic paste. Opposite ends of the wire are preferably provided with electrical terminals or are otherwise exposed to allow for connection to an electric source.

The platinum furnace 110 further contains an amount of platinum catalyst for converting the mixed ammonia ($NH_3$) and C-11 methane ($^{11}CH_4$) gases to C-11 cyanide ($H^{11}CN$) gas. The platinum catalyst is provided as a particulate supported on a substantially chemically non-reactive, heat stable support. The support can be provided in the form of a 3-5 platinum gauze. For example, two platinum gauze pieces, (Product Number: 298107-1.7G), having a 5 cm×5 cm size and totaling about 2-9 grams can be packed in the quartz tube.

However, in a preferred embodiment, the platinum black powder is captured or otherwise supported in a molecular sieve. Thus, a molecular sieve is preferably utilized as the platinum black powder support. Any commercially available 100% platinum black powder can be used. A suitable platinum black catalyst powder is supplied by Engelhard Industries, Inc., 113 Astor Street, Newark, N.J. under for example, Lot #10-077. The molecular sieve preferably has a size of about 4 Angstroms.

It has been surprisingly found that a molecular sieve supporting platinum black provides an efficient means for providing platinum to the high-temperature reaction within the platinum furnace 110. Specifically, the surface area of available platinum is greatly increased by supporting platinum black in the molecular sieve. The lower limit of the amount of platinum black provided in the sieve is determined by the amount sufficient to catalyze the mixed ammonia ($NH_3$) and C-11 methane ($^{11}CH_4$) gases to C-11 cyanide ($H^{11}CN$). The upper limit of the amount of platinum black provided in the sieve is determined by the amount at which platinum coagulation will occur within the platinum furnace tube.

A platinum furnace outlet line 118 is fluidly connected to the platinum furnace outlet for removing reacted C-11 cyanide ($H^{11}CN$) gas from the platinum furnace 110. A two-way solenoid valve 120 and a flow meter 122 are provided in the platinum furnace outlet line 118 to regulate the flow of the C-11 cyanide ($H^{11}CN$) gas from the platinum furnace 110. A three-way solenoid valve 124 is also preferably provided in the platinum furnace outlet line 118 to selectively allow for extraction of the C-11 cyanide ($H^{11}CN$) gas from the system or to divert the C-11 cyanide ($H^{11}CN$) gas back to the three-way solenoid valve 48 provided in the reacted gas lines 12A, 14A, 16A to divert the cyanide gas to the vent 46.

Having described the components of the system 10, operation of the system will now be described in the following EXAMPLE of an actual use of the system, with reference to the drawings.

EXAMPLE

Radioactive C-11 carbon dioxide ($^{11}CO_2$) gas was taken from a target and delivered to the nickel furnace 40 upon the opening of solenoid valves 20, 44, 63 and 64. Once the first radiation detector 56 hit its plateau all valves were closed. Solenoid valves 44 and 24 were then opened to feed hydrogen ($H_2$) gas to the nickel furnace. Once the pressure gage 42 reached 10-15 psi, the solenoid valves 44 and 24 were closed. Nitrogen gas was then introduced at a pressure of about 8.5 psi. This processing step took about 2 minutes.

The nickel furnace 40 was then heated to 450° C. in less than one minute. Once at operating temperature, the carbon dioxide was heated for about 3 minutes to convert the C-11 carbon dioxide ($^{11}CO_2$) gas to C-11 methane ($^{11}CH_4$) gas. During heating, the cooling fan 58 was turned off. Once heating was complete, the solenoid valves 26 and 120 were opened to release the converted C-11 methane ($^{11}CH_4$) gas to the platinum furnace 110, which had been preheated to 950° C. Preheating of the platinum furnace took about 10 minutes.

Ammonia gas was then fed to the system at a pressure of about 6.5 psi. The ammonia gas was mixed with the methane gas in the mixer 90 and was delivered to the platinum furnace. The platinum furnace 110 converted the C-11 methane ($^{11}CH_4$) gas to a product stream containing about 80% C-11 cyanide ($H^{11}CN$) gas. This step took about 2 minutes.

To cool the nickel furnace 40, solenoid valves 24, 44, 63 and 64 were opened to allow hydrogen ($H_2$) to flow. The cooling fan 58 was now turned on until the nickel furnace 40 cooled to below 30° C.

C-11 cyanide ($H^{11}CN$) gas production results utilizing platinum black catalyst powder supported in a molecular sieve are as follows:
Run #1
  1 min beam: 50-70 mCi
  After 9 mins—End of Beam (BOB): 22.4 mCi
Run #2
  After 7 mins—EOB: 24.1 mCi
Run #3
  After 7 mins—EOB: 22.6 mCi Thus, the present system utilizes custom designed furnaces, which are capable of heating to adequate temperatures for both reduction of $CO_2$ (preferably, 420° C.) and formation of C-11 CN (preferably 800-900° C.) within 20 min to be ready for the production from the start. The whole synthesis time is 6 min, which is faster than commercially available systems (about 10 min). Also, the recycle time is 10 min (i.e., every 10 min, another batch of C-11 CN can be produced).

It is also conceivable that the system of the present invention can be equipped with multiple $^{11}CO_2$ (nickel)/$^{11}CH_4$ (platinum) furnaces, which allows more than two productions consecutively without delaying to accommodate a demanding production schedule.

The present system is stand-alone and small enough to be portable (20 cm (D)×28 cm (W)×27 cm (H)), as long as the sources of gases are connected. The product ion control for synthesis can be controlled by one-button (work-away mode) or step-by-step modes. If needed, each valve or furnace can be controlled manually in case of emergency. The control box module (35.5 cm (L)×25.5 cm (W)×8 cm (H)) is connected to a conventional computer. The function of each module is designed to work independently and at the same time, if combined, the whole system works as one integrated production system. The radiochemical yield in the prototypical system is high (60-80%) and production has been shown to be reproducible over 100 times.

As a result of the present system, a cost-effective, stand-alone, and high yielding C-11 cyanide system is provided, which is also very compact and small enough to be workable in a conventional shielded hood of a laboratory. Thus, the small size of the present system requires less lead shielding.

The present system is also highly flexible to produce other C-11 labeled small molecules itself or integrated with the production of other small molecules such as $^{11}CO_2$, C-11 methane, and C-11 carbon monoxide. The system also affords a functional modular design with flexibility for functional combination to produce other C-11 molecules with a short production time and recycling time for production schedule.

Although preferred embodiments of the present invention have been described herein with reference to the accompanying drawings, it is to be understood that the invention is not limited to those precise embodiments and that various other changes and modifications may be affected herein by one skilled in the art without departing from the scope or spirit of the invention, and that it is intended to claim all such changes and modifications that fall within the scope of the invention.

The invention claimed is:

1. A system for producing $H^{11}CN$ gas from $^{11}C$-labeled oxides in less than nine (9) minutes, the system comprising:
   a $^{11}CO_2$ inlet conduit for receiving and conveying $^{11}CO_2$ gas from a target;
   a $H_2$ inlet conduit for receiving and conveying $H_2$ gas from a source;
   a $N_2$ inlet conduit for receiving and conveying $N_2$ gas from a source;
   a heated nickel furnace, said furnace having an entrance and an exit and arranged with a first subzone and a second subzone of substantially all nickel catalyst powder, wherein the first subzone is arranged at said entrance of said heated zone and the second such subzone is arranged at said exit of said heated zone, wherein said first and second subzones sandwich a third subzone which houses a mixture of nickel (Ni) catalyst powder and a molecular sieve, fluidly connected with said $^{11}CO_2$ inlet, said $H_2$ inlet and said $N_2$ inlet for receiving the $^{11}CO_2$ gas, the $H_2$ gas and the $N_2$ gas respectively therefrom, and for heating the $^{11}CO_2$ gas, the $H_2$ gas and the $N_2$ gas in the presence of a nickel catalyst contained within said nickel furnace to produce $^{11}CH_4$ gas;
   a $^{11}CH_4$ conduit connected to an outlet of said nickel furnace for receiving and conveying the $^{11}CH_4$ gas from said nickel furnace;
   a $NH_3$ inlet conduit for receiving and conveying $NH_3$ gas from a source;

a platinum furnace fluidly connected with said $^{11}CH_4$ conduit and said $NH_3$ inlet conduit for receiving the $^{11}CH_4$ gas and the $NH_3$ gas respectively therefrom and for heating the $^{11}CH_4$ gas and the $NH_3$ gas in the presence of a platinum catalyst contained within said platinum furnace to produce $H^{11}CN$ gas; and a $H^{11}CN$ outlet conduit fluidly connected to an outlet of said platinum furnace for receiving and conveying the $H^{11}CN$ gas from said platinum furnace, wherein said $^{11}CO_2$ inlet conduit, said $H_2$ inlet conduit, said $N_2$ inlet conduit, said nickel furnace, said $^{11}CH_4$ conduit, said $NH_3$ inlet conduit, said platinum furnace and said $H^{11}CN$ outlet conduit collectively define a total system gaseous volume of about less than 18 mL whereby the system provides a total system cycle time for producing $H^{11}CN$ gas of less than nine (9) minutes.

2. A system according to claim 1, wherein the system occupies a space less than or equal to about 20 cm×28 cm×27 cm.

3. A system according to claim 1, further comprising a soda lime trap disposed in said $^{11}CH_4$ conduit for removing unreacted $^{11}CO_2$ gas from said $^{11}CH_4$ conduit.

4. A system according to claim 1, further comprising a mixer fluidly connected with said $^{11}CH_4$ conduit and said $NH_4$ inlet conduit for respectively receiving and mixing the $^{11}CH_4$ gas and the $NH_3$ gas from said $^{11}CH_4$ conduit and said $NH_3$ inlet conduit.

5. A system according to claim 1, wherein said nickel furnace further comprises an alumina tube and an electrical resistance heating wire wrapped around said alumina tube, said alumina tube having a length of about 4.5 cm, an outer diameter of about 1.3 cm and an inner diameter of about 9.5 mm.

6. A system according to claim 1, wherein said platinum furnace comprises a quartz tube and an electrical resistance heating wire wrapped around said quartz tube, said quartz tube having a length of about 15 cm, an outer diameter of about 2 cm and an inner diameter of about 1.6 cm.

7. A system according to claim 2 further comprising a second heated nickel furnace fluidly connected via a three-way valve to said heated nickel furnace and said $^{11}CO_2$, $H_2$ and $N_2$ gas inlets.

* * * * *